United States Patent [19]

Urban et al.

[11] Patent Number: 5,102,799
[45] Date of Patent: * Apr. 7, 1992

[54] LIPASE IMMOBILIZED WITH HYDROPHILIZED POLYOLEFIN FIBERS FOR RESOLVING RACEMATES

[75] Inventors: Dieter Urban, Mannheim; Wolfgang Ladner, Fussgoenheim; Axel Paul, Mannheim, all of Fed. Rep. of Germany

[73] Assignee: BASF Aktiengesellschaft, Ludwigshafen, Fed. Rep. of Germany

[ * ] Notice: The portion of the term of this patent subsequent to Jun. 4, 2008 has been disclaimed.

[21] Appl. No.: 267,373

[22] Filed: Nov. 4, 1988

[30] Foreign Application Priority Data

Jun. 8, 1988 [DE] Fed. Rep. of Germany ....... 3819467

[51] Int. Cl.⁵ .................. C12N 11/08; C12N 9/20; C12P 7/64; C12P 7/62
[52] U.S. Cl. .................................... 435/180; 435/134; 435/135; 435/177; 435/182; 435/198; 435/280
[58] Field of Search ............ 435/134, 174, 177, 180, 435/182, 198, 280, 135

[56] References Cited

U.S. PATENT DOCUMENTS

| | | | |
|---|---|---|---|
| 4,451,582 | 5/1984 | Denzinger et al. | 435/188 X |
| 4,629,742 | 12/1986 | Brady et al. | 521/55 |
| 4,732,853 | 3/1988 | Whitesides et al. | 435/198 X |
| 4,767,707 | 8/1988 | Marcinowski et al. | 435/182 |
| 4,798,793 | 1/1989 | Eigtved | 435/198 X |
| 4,818,695 | 4/1989 | Eigtved | 435/180 X |

FOREIGN PATENT DOCUMENTS 0183691 10/1984 Japan ...................... 435/198
0210499 4/1987 Japan .

OTHER PUBLICATIONS

Biotechnology and Bioengineering, vol. XXIV, 1982 pp. 2175-2187, J. Lavayre et al.
Chemical Abstract, vol. 88, No. 21, May 1978, Nr. 147944m, J. S. Patton et al.
Chemical Abstract, vol. 85, No. 23, Dec. 1976, M. M. Rakhimov et al. No. 173493w.
Koho, K. T. Chemical Abstracts, 103:2919a, 1985, p. 274.
Journal of American Chemical Society 1984, 106, pp. 7250-7251, Lipase-Catalysed Hydrolysis as a Route to Esters of Chiral Epoxy Alcohols Wolfgang Ladner, et al.

Primary Examiner—David M. Naff
Attorney, Agent, or Firm—Oblon, Spivak, McClelland, Maier & Neustadt

[57] ABSTRACT

Immobilized lipase is prepared by forming a mixture of hydrophilized polyolefin fibers, crude porcine pancreas lipase, one or more water soluble dihydric to hexahydric aliphatic alcohols of 2 to 6 carbons and an aqueous buffer solution of pH 5-9 at a temperature of 0° to 40° C., allowing the mixture to stand for 1 minute to 3 days, filtering the mixture and washing the resultant filter cake. The dihydric to hexahydric alcohol may be combined with one or more water soluble monohydric alcohols having 1 to 4 carbon atoms. The immobilized lipase is used for resolving racemates of esters of racemic alcohols in an aqueous medium.

15 Claims, No Drawings

LIPASE IMMOBILIZED WITH HYDROPHILIZED POLYOLEFIN FIBERS FOR RESOLVING RACEMATES

The present invention relates to a simple and economical process for the preparation of an immobilisate of crude pancreas lipase based on a hydrophilized polyolefin fiber, the immobilisate itself and its use for resolving the racemates of esters of racemic alcohols.

Techniques for immobilizing lipase are known. According to U.S. Pat. No. 4,629,742, lipase from Candida cylindracea is used for immobilization, and hydrophobic, microporous polymers prepared by a very expensive process are used as a substrate.

The immobilization process described in EP-A-210 499, for, inter alia, pancreas lipase and comprising gel formation from enzyme, polyepoxide and polyamine is simple but leads to biocatalysts which have low mechanical stability and poor hydrodynamic properties (filterability, flow resistance in columns packed with the biocatalyst) and are therefore not very suitable for industrial use.

The enantioselective resolution of racemic esters by porcine pancreas lipase on the laboratory scale is also known (W. E. Ladner and G. M. Whitesides, J. Amer. Chem. Soc. 106 (1984), 7250-7251). Crude, non-immobilized lipase is used in this method. This process is not suitable for use industrially, an economical process requiring immobilization. Immobilization employing conventional methods, for example according to the abovementioned U.S. Patent, did not give the desired result since the specific activity of the immobilisate was low and decreased far too rapidly during operation.

It is an object of the present invention to prepare immobilisates of crude pancreas lipase by a simple and economical method, making it possible to carry out a simple and economical process for the resolution of racemates of esters of optically active alcohols which is suitable for the industrial scale. Important criteria of a suitable biocatalyst are a long life and high space-time yields.

We have found that this object is achieved by a process as claimed in claims 1 to 9. The biocatalyst is prepared by mixing a hydrophilized polyolefin fiber, a lipase and water at pH 5-9, preferably 5.5-8, and at from 0° to 40° C., preferably from 10° to 30° C., filtering the mixture after from 1 minute to 3 days, preferably from 1 to 24 hours, and washing the filter cake with water or a buffer solution or a water-soluble organic solvent, wherein the lipase used is commercial porcine pancreas lipase which is crude, i.e. contains up to 99% by weight of natural impurities (especially proteins), and is therefore very readily and economically available, and one or more water-soluble aliphatic alcohols having 2 to 6 carbon atoms and 2 to 6 hydroxyl groups, if required as a mixture with a monohydric alcohol of 1 to 4 carbon atoms, is added to the aqueous mixture as a stabilizer for the lipase (to prolong its activity).

Polyolefins are polyethylene, polypropylene and their mixtures and copolymers.

Hydrophilization (to improve the wettability with water) can be effected by one of the following methods:

1. The ready-prepared fibers can be treated with a hydrophilizing agent, for example with polyvinyl alcohol (according to German Patent 2,237,606) or with a melamine/formaldehyde polycondensate (according to German Patent 2,346,081 or 2,545,727).

2. In the preparation of the fibers, for example according to German Published Application DAS 2,117,370, the hydrophilizing agent (for example one of those mentioned above) can be added to the polyolefin solution so that the hydrophilizing agent is mechanically incorporated into the fibers (cf. for example German Laid-Open Application DOS 2,208,553).

3. Copolymerization of the fiber-forming olefin with hydrophilic comonomers, such as vinyl acetate (with subsequent hydrolysis), N-vinylformamide, n-butyl acrylate, acrylic acid or acrylamide (cf. for example U.S. Pat. No. 4,210,615).

Synthetic polyethylene pulp from Schwarzwälder Textilwerke, D-7623 Schenkenzell, has proven particularly useful.

The mean length of the polyolefin fibers should be from 0.05 to 10 mm, preferably from 0.1 to 4 mm, depending on the particular use. The lower limit is determined by the filterability and the hydrodynamic resistance of a column packed with the said fibers. The ratio of length to diameter is not less than 5:1 and is in general from 10:1 to 20:1. The amount of the hydrophilizing additives used to achieve better wetting with water is from 0.1 to 10%, preferably from 0.4 to 4%, based on the fiber weight.

Although the lipase itself is water-soluble, many components of the crude lipase are water-insoluble and are suspended in the reaction mixture.

Water-soluble alcohols are those which have a water solubility of not less than 10, preferably not less than 20, % by weight at 20° C. Particularly preferred alcohols are those which are infinitely miscible with water. The hydricity of the alcohol means the number of hydroxyl groups. Examples of suitable water-soluble alcohols are: ethylene glycol, 1,2- and 1,3-propanediol, 1,2-, 1,3-, 1,4- and 2,3-butanediol, 1,2- and 1,3-isobutanediol, 1,2- and 1,5-pentanediol, diethylene glycol, glycerol, erythritol, pentaerythritol, arabitol, xylitol, sorbitol, mannitol and dulcitol and mixtures of these. Some of these polyhydric alcohols can also be replaced by one or more of the following monohydric alcohols: methanol, ethanol, 1- and 2-propanol, 2-butanol and tert-butanol. Polyhydric water-soluble alcohols having 2 to 6 OH groups alone or as mixtures with alcohols of various hydric states, in particular glycerol and mixtures of glycerol with methanol, ethanol, 1,5-pentanediol and in particular 2-propanol, are preferred.

To bring the pH to 5-9, preferably 5.5-8, it is expedient to use the conventional buffer mixtures, for example mixtures of primary and secondary phosphates, borax, mixtures of tris-(hydroxymethyl)-methylamine and its hydrochloride, and acetate buffer mixtures.

The total mixture has the following composition:
from 1 to 50, preferably from 2 to 30, % of hydrophilized polyolefin fibers,
from 1 to 30, preferably from 5 to 25, % of crude porcine pancreas lipase,
from 1 to 68, preferably from 20 to 60, % of one or more of the water-soluble, polyhydric alcohols described, where the amount above 1, preferably above 5, in particular 10, % can be replaced by a water-soluble monohydric alcohol of 1 to 4 carbon atoms,
from 30 to 97% of water
and the pH-regulating additives (whose weight is scarcely significant). The percentages are all based on the weight of the total mixture.

The components can be mixed in any order; preferably, the crude lipase is suspended in a mixture of water and alcohol, and the fibers are then added.

The mixture is advantageously left for from 1 minute to 3 days, preferably from 1 hour to 1 day, at from 0° to 40° C., preferably from 10° to 30° C., and is preferably kept in motion (e.g. stirring or rolling). It is then filtered. The washed or unwashed filter cake can be used directly in an aqueous medium for resolution of esters. However, it is advantageously treated, i.e. brought into contact, beforehand with an aqueous or aqueous alcoholic solution of a crosslinking agent for from 1 minute to 2 hours, preferably from 2 minutes to 1 hour, at room temperature (from 10° to 30°) in order to fix the lipase. Examples of suitable crosslinking agents are dialdehydes, in particular glutardialdehyde and glyoxal, as well as water-soluble glycidyl ethers, prepared according to EP-A 210 499 by an addition reaction of from 1 to 30 equivalents of an epoxide of the formula I

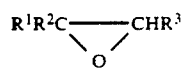    I where $R^1$, $R^2$ and $R^3$ are each hydrogen, methyl or ethyl, with in each case one equivalent (based on OH groups) of a polyfunctional alcohol of 2 to 6 carbon atoms or of a mono- or disaccharide and reaction of the resulting adduct with one equivalent of epichlorohydrin per OH group, followed by cyclization to give the epoxide.

Although crosslinking has a somewhat adverse effect on the initial activity, for which reason excessive crosslinking should be avoided, the activity remains relatively stable on repeated use (Examples 1, 2 and 5).

The immobilisate can be used in a conventional manner, for example in columns or in a stirred reactor.

The novel process is the first one to make it possible to convert porcine pancreas lipase into a reusable, readily filterable immobilisate which is suitable for use in columns and has high specific activity and a long useful life. The fact that impurities in crude lipase do not present problems makes the process particularly economical. Determination of the enzymatic activity of pancreatin In a pH-stat apparatus, 50 ml of borax/HCl buffer (20 mM, pH 7.5) and 1 ml of glycidyl butyrate are mixed with one another and the mixture is stirred thoroughly at 30° C. After the addition of a suitable amount (usually 1-10 mg) of crude pancreas lipase or of the immobilisate to be tested (500 mg), the pH is kept constant by automatic metering of 0.5N NaOH solution. The specific enzymatic activity Asp is calculated as follows:

$$A_{sp} = \frac{\Delta V \cdot N}{\Delta t \cdot m}$$

$\Delta V/\Delta t$ is the amount of sodium hydroxide solution consumed at the beginning of the reaction in ml/min, N is the normality of the sodium hydroxide solution (500 µmol/ml) and m is the amount of enzyme or of immobilisate weighed in.

The usual unit for the enzymatic activity is 1 unit (abbreviation: u), corresponding to an NaOH consumption of 1 µmol/min.

The specific activity of the Nordmark pancreatin used for the immobilization was 17 u/mg.

In the Examples which follow, parts and percentages are by weight. Resolution of the esters was carried out using glycidyl butyrate in every case. Preparation of the immobilisate

EXAMPLE 1

2 g of crude porcine pancreas lipase were suspended in 18 g of a mixture of 80 parts of 200 millimolar phosphate buffer solution of pH 7.0, 10 parts of glycerol and 10 parts of isopropanol. 1 g of synthetic polyethylene pulp SWP ESS 21F from Schwarzwälder Textilwerke Schenkenzell, consisting of 0.5 g of polyethylene fibers (mean fiber length 0.6 mm, polyvinyl alcohol content 4%) and 0.5 g of water, was added to this suspension. The mixture was stirred overnight, after which 5.4 g of glutardialdehyde (25% strength in water) were added. The mixture was stirred for a further hour, after which it was filtered and the residue was washed with a mixture of 80 parts of 200 millimolar phosphate buffer solution of pH 7.0, 10 parts of glycerol and 10 parts of isopropanol and sucked off thoroughly. 2.0 g of immobilisate were obtained. This was used five times for resolution of esters, and the specific enzymatic activities are shown in the Table:

| Batch | $A_{sp}$ [u/g] | $A_{rel}$ (in %) |
|---|---|---|
| 1 | 1,449 | — |
| 2 | 1,307 | 90 |
| 3 | 1,212 | 84 |
| 4 | 1,111 | 77 |
| 5 | 1,026 | 71 |

$A_{sp}$ = specific activity in u/g
$A_{rel}$ = relative activity, based on the original activity

EXAMPLE 2

The procedure was similar to that of Example 1, but without crosslinking with glutardialdehyde. 2.4 g of immobilisate were obtained.

| Batch | $A_{sp}$ [u/g] | $A_{rel}$ (in %) |
|---|---|---|
| 1 | 3,700 | — |
| 2 | 2,381 | 64 |
| 3 | 1,498 | 40 |
| 4 | 1,149 | 31 |
| 5 | 828 | 22 |

The procedure was similar to that of Example 1, except that half the amount of porcine pancrease lipase was used. 1.9 g of immobilisate were obtained.

| Batch | $A_{sp}$ [u/g] | $A_{rel}$ (in %) |
|---|---|---|
| 1 | 1,333 | — |
| 2 | 1,093 | 82 |
| 3 | 950 | 71 |
| 4 | 910 | 68 |
| 5 | 901 | 68 |

The procedure was the same as that of Example 1, except that only a quarter of the amount of porcine pancreas lipase was used. 1.7 g of immobilisate were obtained.

| Batch | $A_{sp}$ [u/g] | $A_{rel}$ (in %) |
|---|---|---|
| 1 | 606 | — |
| 2 | 513 | 85 |
| 3 | 476 | 79 |
| 4 | 427 | 70 |
| 5 | 416 | 69 |

EXAMPLE 5

The procedure was the same as that of Example 1, except that half the amount of glutardialdehyde was used. 2.1 g of immobilisate were obtained.

| Batch | $A_{sp}$ [u/g] | $A_{rel}$ (in %) |
|---|---|---|
| 1 | 2,516 | — |
| 2 | 2,469 | 98 |
| 3 | 2,381 | 95 |
| 4 | 2,150 | 85 |
| 5 | 2,083 | 83 |

EXAMPLE 6

1 g of crude porcine pancreas lipase was suspended in 18 g of a mixture of 65 parts of 50 millimolar borate buffer solution of pH 8.0, 30 parts of glycerol and 5 parts of ethanol. 1 g of synthetic polyethylene pulp SWP E-780 from the company stated in Example 1, consisting of 0.35 g of polyethylene fibers (mean fiber length 1.6 mm, polyvinyl alcohol content 0.4%) and 0.65 g of water, was added to this suspension. The mixture was stirred for 3 hours, after which 2.5 g of sorbitol-EO$_{80}$ epoxide (see below) were added and stirring was continued for a further hour. The immobilisate was filtered off under suction and washed with the above mixture of borate buffer, glycerol and ethanol. 2.6 g of immobilisate were obtained. This was used three times for resolution of esters, and the specific activities are shown in the Table.

| Batch | $A_{sp}$ [u/g] | $A_{rel}$ (in %) |
|---|---|---|
| 1 | 1,010 | — |
| 2 | 960 | 95 |
| 3 | 814 | 81 |

The sorbitol-EO$_{80}$ epoxide had an epoxide value of 1.2 mmol/g and was prepared as follows (German Patent 3,527,014):

14.8 g of BF$_3$ dihydrate are added to 3,705 g of sorbitol-EO$_{80}$ (reaction product of 1 mole of sorbitol with 80 moles of ethylene oxide; cf. Houben-Weyl, Methoden der Org. Chemie 14/2 (1963), page 450). 555 g of epichlorohydrin are then added dropwise at 70° C., while stirring. Stirring is continued for a further 2 hours at 70° C., after which 528 g of 50% strength sodium hydroxide solution are added dropwise in the course of from 1 to 2 hours at from 20° to 35° C. Stirring is continued until about 90% of the sodium hydroxide solution have been consumed. Consumption of the sodium hydroxide solution was monitored titrimetrically.

The major part of the water is distilled off at 70° C. under reduced pressure from a water pump, and the residue is sucked off at elevated temperatures (70° C.).

In this way, 3,439 g (85%) of the reaction product of epichlorohydrin with sorbitol-EO$_{80}$ are obtained, this product having an epoxide titer of 1.2 mmol/g.

EXAMPLE 7

2 g of crude porcine pancreas lipase were suspended in 18 g of a mixture of 200 millimolar phosphate buffer solution of pH 8.0 and alcohol (cf. Table). 1 g of synthetic polyethylene pulp SWP E-790 from the abovementioned company, consisting of 0.5 g of polyethylene fibers (mean fiber length 1.6 mm, polyvinyl alcohol content 0.7%) and 0.5 g of water, was added to this suspension. This mixture was stirred overnight, 2.7 g of glutardialdehyde (25% strength in water) were added and stirring was continued for 1 hour. The immobilisate was filtered off under suction and washed with the particular alcohol/phosphate buffer solution.

| Alcohol [Parts by wt.] | Phosphate buffer [Parts by weight] | Batch | $A_{sp}$ [u/g] | $A_{rel}$ in % |
|---|---|---|---|---|
| — | Glycerol 12 | 88 | 1 | 833 | — |
|  |  |  | 2 | 833 | 100 |
| Isopropanol 10 | Glycerol 20 | 80 | 1 | 2469 | — |
|  |  |  | 2 | 2083 | 84 |
| 1,5-pentane-diol 10 | Glycerol 10 | 80 | 1 | 1546 | — |
|  |  |  | 2 | 1380 | 89 |
| Methanol 10 | Glycerol 10 | 80 | 1 | 1050 | — |
|  |  |  | 2 | 940 | 90 |

EXAMPLE 8

60 g of crude porcine pancreas lipase were suspended in 540 g of a mixture of 80 parts of 200 millimolar phosphate buffer solution of pH 7.0, 10 parts of glycerol and 10 parts of isopropanol. 30 g of synthetic polyethylene pulp SWP ESS 21F from the abovementioned company, consisting of 15 g of polyethylene fibers (mean fiber length 0.6 mm, polyvinyl alcohol content 4%) and 15 g of water, were added to this suspension. The mixture was rolled overnight, after which 81 g of glutardialdehyde (25% strength in water) were added. After stirring had been continued for a further hour, the mixture was filtered and the residue was washed with 810 g of the abovementioned mixture of 80 parts of phosphate buffer solution, 10 parts of glycerol and 10 parts of isopropanol and was sucked off thoroughly. 82 g of immobilisate having a specific activity of 2469 u/g at 30° C. were obtained. This immobilisate was employed in the Use Example.

COMPARATIVE EXPERIMENT 1 (with a different substrate)

2 g of crude porcine pancreas lipase were suspended, according to EP-A-210 499, in 8 g of a solution of parts of 50 millimolar phosphate buffer of pH 8.0 and parts of glycerol, and the suspension was mixed with 6.5 g of sorbitol-EO$_{80}$ epoxide (cf. Example 6) and 4.0 g of polyethyleneimine solution (25% strength in water, brought to pH 8.0 with HCl). After 24 hours, the resulting gel was forced through a sieve having a mesh size of 1 mm.

| Batch | $A_{sp}$ [u/g] | $A_{rel}$ (in %) |
|---|---|---|
| 1 | 53 | 100 |

-continued

| Batch | $A_{sp}$ [u/g] | $A_{rel}$ (in %) |
|---|---|---|
| 2 | 32 | 60 |
| 3 | 28 | 53 |

COMPARATIVE EXPERIMENT 2 (with a different substrate)

2 g of crude porcine pancreas lipase were suspended in 18 g of a mixture of 80 parts of 200 millimolar phosphate buffer solution of pH 8.0, 10 parts of glycerol and 10 parts of isopropanol. 1 g of porous polyethylene, prepared according to U.S. Pat. No. 4,247,498 (Accurel® HDPE powder, Enka AG, Wuppertal), was added to this suspension and the mixture was stirred overnight. 1 hour after the addition of 5.4 g of glutardialdehyde (25% strength in water), the product was filtered off under suction. 2.1 g of immobilisate were obtained.

| Batch | $A_{sp}$ [u/g] | $A_{rel}$ (in %) |
|---|---|---|
| 1 | 120 | 100 |
| 2 | 73 | 61 |

COMPARATIVE EXPERIMENT 3

The procedure was similar to that of Example 5, except that the alcohol was replaced by phosphate buffer solution of pH 8.0.

| Batch | $A_{sp}$ [u/g] | $A_{rel}$ (in %) |
|---|---|---|
| 1 | 470 | 100 |
| 2 | 439 | 93 |
| 3 | 388 | 83 |
| 4 | 384 | 82 |
| 5 | 328 | 70 |

COMPARATIVE EXPERIMENT 4

Four other lipases were used, similarly to Example 1:

Lipase Saiken 100 from Rhizopus japonicus, from K.K. Osaka Saihin Kenkyusho
Lipase M-AP 10 from Mucor sp., from Amano Pharmaceutical Co. Ltd.
Piccantase A from Mucor miehei, from Gist-Brocades
Lipase My from Candida cylindracea, from Meito Sangyo.

The first three had no enzymatic activity in the resolution of esters; the specific activities of the lipase My are shown in the Table:

| Batch | $A_{sp}$ [u/g] | $A_{rel}$ (in %) |
|---|---|---|
| 1 | 399 | — |
| 2 | 280 | 70 |

USE EXAMPLE 1.4 l of a 0.05 molar buffer solution brought to pH 7 ($Na_2B_4O_7 \cdot 10H_2O$ adjusted with concentrated hydrochloric acid) were cooled to 6° C. 216.1 g (1.5 moles) of racemic glycidyl butyrate and 10 g of moist immobilisate from Example 8, washed with pH 7 buffer solution, were added. The mixture was stirred thoroughly at from 9 to 10° C. and kept at about pH 7.3 by pumping in 10 N NaOH (a total of 82.5 ml, 0.825 mole, corresponding to 55% hydrolysis). After 130 minutes, the stated amount of NaOH had been consumed. The immobilisate was filtered off, washed twice with $CH_2Cl_2$ and once with pH 8 buffer and then suspended in pH 7 buffer and kept at from 5° to 8° C. The filtrate and the wash phases were combined and shaken thoroughly, and the organic phase was separated off. The aqueous phase was extracted three times more with $CH_2Cl_2$. The combined organic phases were dried over sodium sulfate and evaporated down under reduced pressure in a rotary evaporator, and the residue was distilled. 78 g of R(−) glycidyl butyrate were obtained (0.55 mole, 80% yield, based on the 0.67 mole of R(−) glycidyl butyrate theoretically obtainable at 55% hydrolysis). Angle of rotation $[\alpha]^{D}_{20} = 30.00°$, bp. 83° C./ 14 mbar.

The immobilisate could be used repeatedly, the activity decreasing slowly and substantially stabilizing at about 70%.

What is claimed is:

1. A process for the preparation of an immobilized lipase, which comprises:
    a) mixing a substrate of hydrophilized polyolefin fibers, a crude porcine pancreatic lipase, an aqueous buffer solution at pH 5-9 and one or more water-soluble polyhydric aliphatic alcohols having from 2 to 6 carbon atoms and from 2 to 6 hydroxyl groups at a temperature of from 0° to 40° C., and allowing the mixture to stand from 1 minute to 3 days, and
    b) filtering the mixture to produce a filter cake, and washing the cake, to obtain said immobilized lipase.

2. The process as claimed in claim 1, wherein said one or more water-soluble polyhydric aliphatic alcohols have further added thereto one or more water-soluble monohydric alcohols having from 1 to 4 carbon atoms.

3. The process as claimed in claim 2, wherein said polyhydric aliphatic alcohol is glycerol or 1,5-pentanediol or a mixture thereof, and said monohydric alcohol is selected from the group consisting of methanol, ethanol and isopropanol.

4. The process as claimed in claim 1, wherein the mixture contains from 1 to 50% of hydrophilized polyolefin fibers, from 1 to 30% of crude porcine pancreatic lipase and from 1 to 68% of said one or more water-soluble polyhydric aliphatic alcohols, and said mixture further containing pH-regulating additives.

5. The process as claimed in claim 4, wherein over 10% of said one or more water-soluble polyhydric alcohols is replaced with said one or more water-soluble monohydric alcohols.

6. The process as claimed in claim 2, wherein a mixture of the polyolnic alcohol, glycerol, and the monohydric, isopropanol, is used as the water-soluble alcohol.

7. The process as claimed in claim 1, wherein the filter cake is treated with a crosslinking agent.

8. The process as claimed in claim 7, wherein glutardialdehyde is used as the crosslinking agent.

9. The process as claimed in claim 7, wherein the crosslinking agent used is a water-soluble glycidyl ether which is prepared by an addition reaction of from 1 to 30 equivalents of an epoxide of the formula:

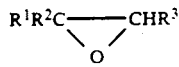

wherein $R^1$, $R^2$ and $R^3$ are each hydrogen, methyl or ethyl, with one equivalent, of a polyfunctional alcohol of 2 to 6 carbon atoms or of a mono- or disaccharide, whereby an adduct is formed, and reacting said adduct with 1 mole of epichlorohydrin per equivalent of OH groups, followed by cyclization to give the epoxide.

10. The process as claimed in claim 1, wherein said polyolefin fibers are fibers of polyethylene, polypropylene and mixtures thereof and copolymers thereof.

11. The process as claimed in claim 11, wherein said polyolefin fibers have a mean length of from 0.05 to 10 mm, and have a ratio of length to diameter of not less than 5:1.

12. The process as claimed in claim 1, wherein said polyolefin fibers are hydrophilized by adding a hydrophilizing additive in the amount of 0.1 to 10% by wt. based on the fiber weight.

13. An immobilized lipase prepared by the process of claim 1.

14. A process for resolving a racemate of an ester of a racemic alcohol in an aqueous medium which comprises:
   a) preparing an immobilized lipase by: mixing a substrate of hydrophilized polyolefin fibers, a crude porcine pancreatic lipase, an aqueous buffer solution at pH 5-9 and one or more water-soluble polyhydric aliphatic alcohols having from 2 to 6 carbon atoms and from 2 to 6 hydroxyl groups at a temperature of from 0° to 40° C., and allowing the mixture to stand from 1 minute to 3 days to obtain said immobilized lipase;
   b) mixing said racemate with said immobilized lipase; and
   c) isolating resolved racemate from the immobilized lipase.

15. The process as claimed in claim 14, wherein said racemate is a racemate of glycidyl butyrate.

* * * * *